(12) United States Patent
Song

(10) Patent No.: US 9,757,215 B2
(45) Date of Patent: Sep. 12, 2017

(54) DENTAL SINUS LIFT DEVICE FOR IMPLANT REHABILITATION

(71) Applicant: Froncare, Bayside, NY (US)

(72) Inventor: Jun Song, Bayside, NY (US)

(73) Assignee: FRONCARE, Bayside, NY (US)

( * ) Notice: Subject to any disclaimer, the term of this patent is extended or adjusted under 35 U.S.C. 154(b) by 136 days.

(21) Appl. No.: 14/487,377

(22) Filed: Sep. 16, 2014

(65) Prior Publication Data

US 2016/0074140 A1    Mar. 17, 2016

(51) Int. Cl.
*A61B 18/18*    (2006.01)
*A61C 8/00*    (2006.01)

(52) U.S. Cl.
CPC .................. *A61C 8/0092* (2013.01)

(58) Field of Classification Search
USPC ............................................ 606/48; 433/173
See application file for complete search history.

(56) References Cited

U.S. PATENT DOCUMENTS

| | | | |
|---|---|---|---|
| 7,249,949 B2 * | 7/2007 | Carter | A61C 8/005 433/173 |
| 8,083,747 B2 | 12/2011 | Song | |
| 8,377,064 B2 | 2/2013 | Wallis | |
| 8,556,627 B2 | 10/2013 | Better et al. | |
| 2005/0287497 A1 * | 12/2005 | Carter | A61C 8/005 433/173 |
| 2007/0037121 A1 * | 2/2007 | Carter | A61C 8/0089 433/173 |
| 2008/0319466 A1 | 12/2008 | Eder | |
| 2009/0181345 A1 | 7/2009 | Kfir | |
| 2010/0324561 A1 | 12/2010 | Watzek | |
| 2011/0097688 A1 * | 4/2011 | Rebaudi | A61C 8/0018 433/174 |
| 2014/0038126 A1 | 2/2014 | Pavel Krastev | |

FOREIGN PATENT DOCUMENTS

| | | |
|---|---|---|
| KR | 20100025706 | 3/2010 |
| KR | 30-0673995 | 12/2012 |
| KR | 30-0703331 | 10/2013 |

OTHER PUBLICATIONS

Virgilio Mongalo, DMD et al, Study reveals how automated patient appointment reminders affect dental practice no-show rates and production et al, Dental Tribune U.S., vol. 8-18, No. 2, Feb. 2013 et al.

* cited by examiner

*Primary Examiner* — Nicole F Johnson
(74) *Attorney, Agent, or Firm* — Lex IP Meister, PLLC

(57) ABSTRACT

A dental device comprises a distal part having a first lateral hole formed on a lateral side of the distal part; a middle part connected to the distal part; and a proximal part connected to the middle part, wherein the dental device has a central lumen penetrating the proximal part, the middle part, and the distal part and communicating to the first lateral hole and wherein the distal part has an exit of the central lumen at a distal end and the proximal part has an entrance of the central lumen at a proximal end.

16 Claims, 14 Drawing Sheets though the bone bore, from the osteotomy, into the cavity of the mouth. Then, bone graft material of operator's choice is injected through the bone bore to fill the sinus cavity.

DENTAL SINUS LIFT DEVICE FOR IMPLANT REHABILITATION

BACKGROUND (a) Technical Field

The present specification relates to a dental device for sinus lift which is applied in implant rehabilitation.

(b) Description of the Related Art

Implant rehabilitation of the edentulous posterior maxilla is a challenging procedure in the presence of insufficient bone volume and especially height, for implant placement.

Maxillary sinus elevation technique is a common surgical procedure which allows augmentation of the available bone volume in posterior maxilla in order to place implants.

To increase the bone volume in the posterior maxilla, the sinus lift procedure has been developed since the mid-1970s. There are two well accepted techniques to treat the loss of vertical bone height in the posterior maxilla. First is the lateral window technique and second is the crestal approach sinus lift technique.

Many dentists prefer the crestal approach technique, because it is a less invasive procedure. The crestal approach technique typically uses saline solution and hydraulically lifts the membrane. When the saline solution is under pressure, it causes the maxillary sinus membrane to be elevated from the bone. Sufficient volume of saline solution is introduced so that the sinus cavity with sufficient volume is formed. Saline that has been used to elevate the sinus membrane is evacuated before regenerative material is introduced into sinus cavity.

Prior arts disclose technique where, as the sinus cavity is filled with saline solution, after extracting the device that introduces the saline solution from the bone bore, the patient is asked to exert pressure, such as, by sneezing while the patient's nose is held, thereby causing excess pressure in the maxillary sinus by which the saline solution is drained through the bone bore, from the osteotomy, into the cavity of the mouth. Then, bone graft material of operator's choice is injected through the bone bore to fill the sinus cavity.

SUMMARY

The present exemplary embodiments have been made in an effort to provide a dental device that allow sequential processing of introducing a fluidal material such as a saline solution, draining the fluidal material, and injecting a regenerative material without extracting the dental device.

An exemplary embodiment of the present invention provides a dental device comprising: a distal part having a first lateral hole formed on a lateral side of the distal part; a middle part connected to the distal part; and a proximal part connected to the middle part, wherein the dental device has a central lumen penetrating the proximal part, the middle part, and the distal part and communicating to the first lateral hole and wherein the distal part has an exit of the central lumen at a distal end and the proximal part has an entrance of the central lumen at a proximal end.

The distal part may further have a second lateral hole disposed opposite to the first lateral hole and communicating to the central lumen.

The distal part may comprise a screw thread on an outer surface of the distal part.

The first and second lateral holes may have a shape among a circle, an oval, a square and a square with rounded corners.

Diameter of the distal part may be smaller around the distal end and the first and second lateral holes than the other portion.

The distal part around the lateral holes may be rounded or gently trimmed to form a non-cutting edge.

The first and second lateral holes may be disposed in 1 mm~5 mm from the distal end.

The proximal part may have a plurality of loop protrusions on an outer surface of the proximal part.

The loop protrusions may have asymmetric slopes.

The middle part may comprise at least one multiple sided nut portion and a stopper protrusion.

The stopper protrusion may have a larger diameter than the other portions of the dental device and may be disposed closer from the distal part than the at least one multiple sided nut portion.

The middle part may comprise two multiple sided nut portions and a first groove disposed between the two multiple sided nut portions.

The dental device may further comprise a first silicon ring put on the first groove.

The dental device may further comprise a second silicon ring put on a second groove disposed between the distal part and the stopper protrusion.

The distal part, the middle part, and the proximal part may be integrally formed.

Another embodiment provides a dental device comprising: a distal part having a plurality of lateral holes formed on a lateral side of the distal part and a screw thread formed on an outer surface of the distal part; a middle part connected to the distal part and having a stopper protrusion and at least one multiple sided nut portion; and a proximal part connected to the middle part, wherein the dental device has a central lumen penetrating the proximal part, the middle part, and the distal part and communicating to the plurality of lateral holes.

DETAILED DESCRIPTION OF THE EMBODIMENTS

Exemplary embodiments will be described more fully hereinafter with reference to the accompanying drawings, in which exemplary embodiments of the present invention are shown. As those skilled in the art would realize, the described embodiments may be modified in various different ways, all without departing from the spirit or scope of the embodiments.

Figure 1:
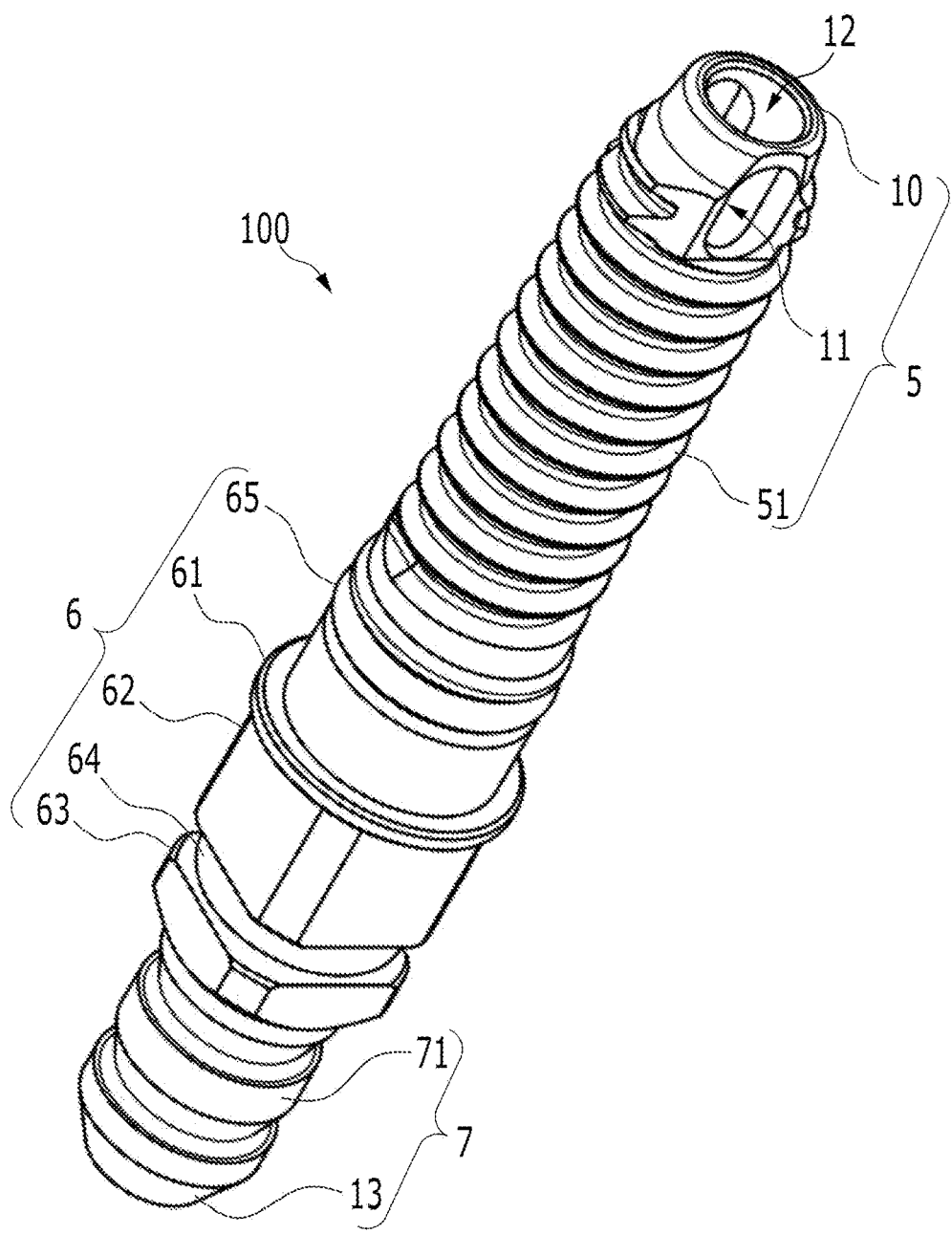
FIG. 1 is a perspective view of a dental device according to an exemplary embodiment of the present invention.
Figure 2:
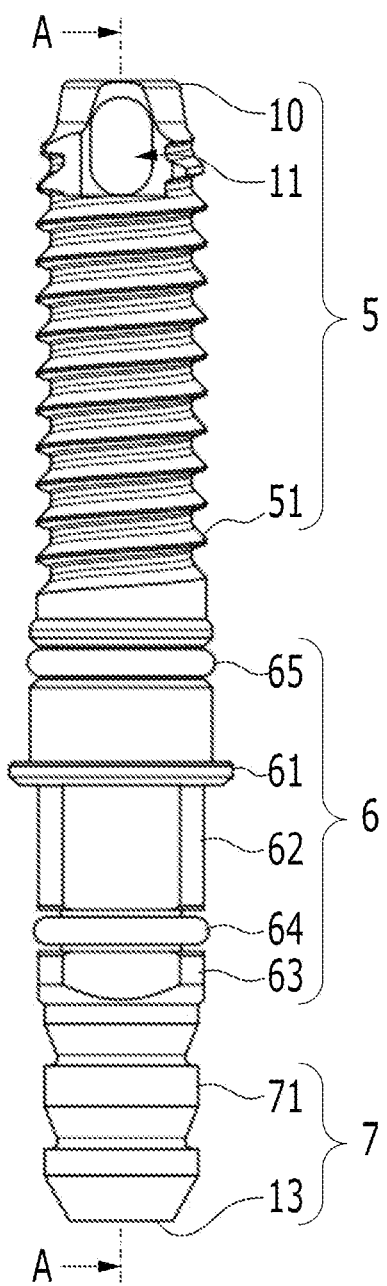
FIG. 2 is a first side view of the dental device of FIG. 1.
Figure 3:
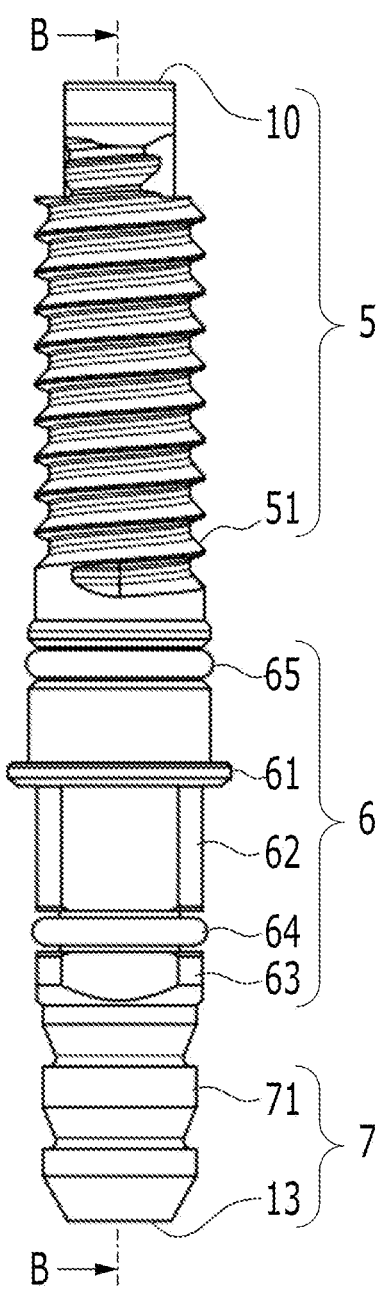
FIG. 3 is a second side view of the dental device of FIG. 1.
Figure 4:
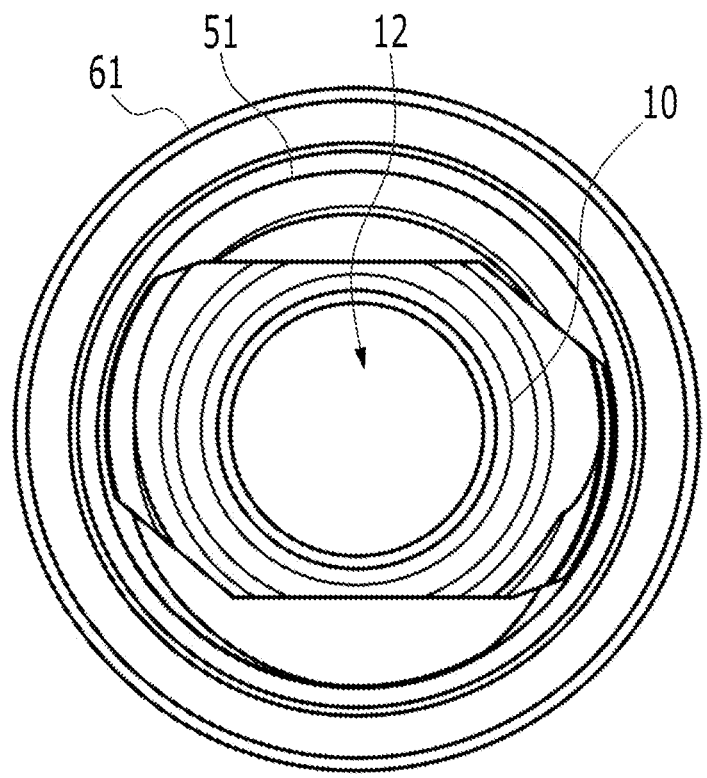
FIG. 4 is a top view of the dental device of FIG. 1.
Figure 5:
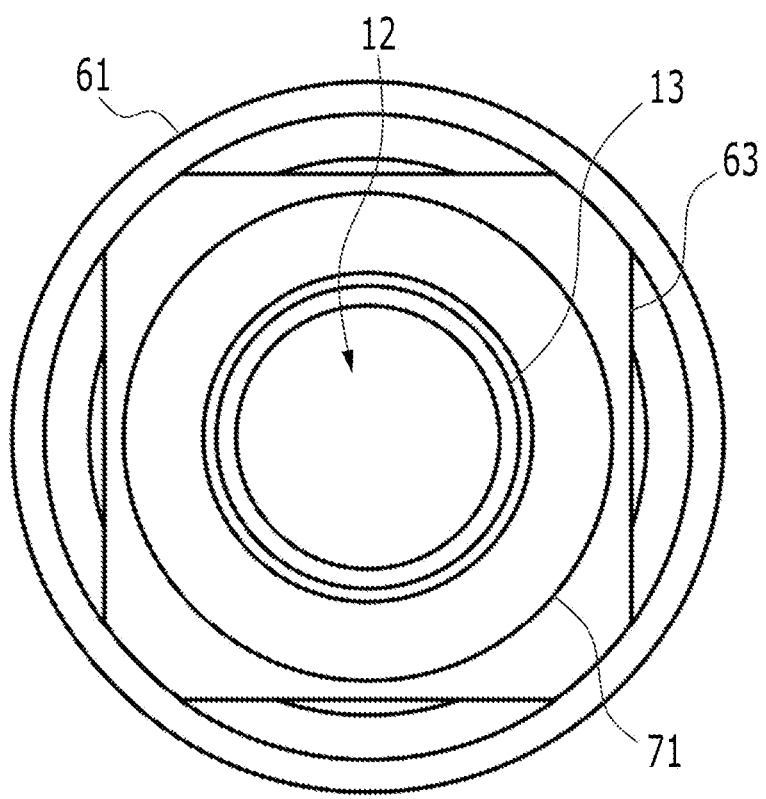
FIG. 5 is a bottom view of the dental device of FIG. 1.
Figure 6:
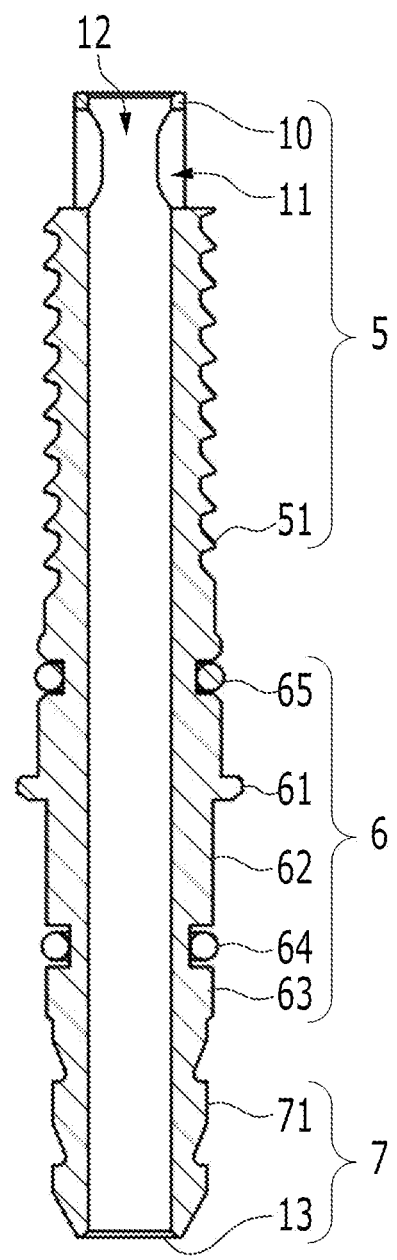
FIG. 6 is a cross-sectional view of the dental device shown in the direction of A-A of FIG. 2.
Figure 7:
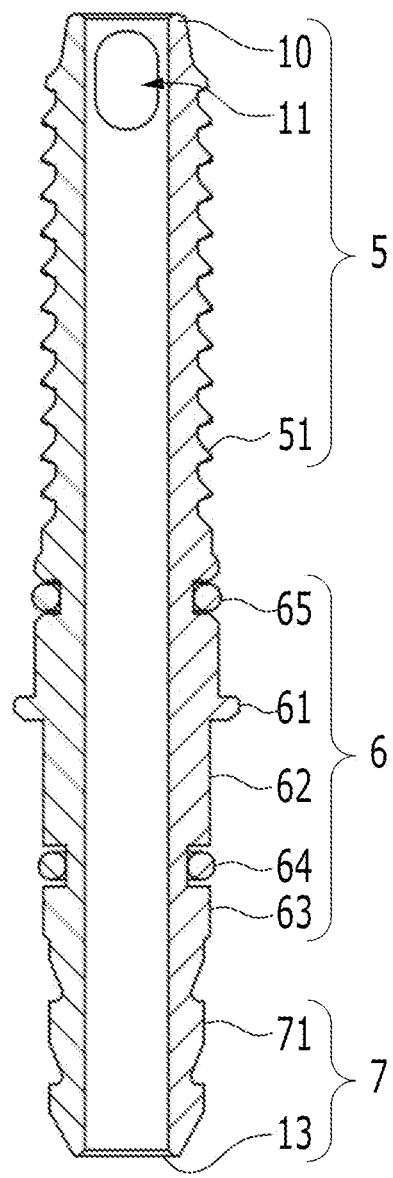
FIG. 7 is a cross-sectional view of the dental device shown in the direction of B-B of FIG. 3

FIG. 1 is a perspective view of a dental device according to an exemplary embodiment of the present invention. FIG. 2 is a first side view of the dental device of FIG. 1. FIG. 3 is a second side view of the dental device of FIG. 1. FIG. 4 is a top view of the dental device of FIG. 1. FIG. 5 is a bottom view of the dental device of FIG. 1. FIG. 6 is a cross-sectional view of the dental device shown in the direction of A-A of FIG. 2. FIG. 7 is a cross-sectional view of the dental device shown in the direction of B-B of FIG. 3

Referring FIGS. 1-7, a dental device 100 according to an exemplary embodiment of the present invention comprises a distal part 5, a proximal part 7 and an middle part 6. The dental device 100 has a central lumen 12 penetrating the dental device 100 along the vertical axis of the dental device 100. Therefore, the central lumen 12 has an entrance at the proximal end 13 of the dental device 100 and an exit at the distal end 10 of the dental device 100. The dental device 100 may be formed of a metal such as titanium or an alloy such as stainless steel. The dental device 100 may be formed of a plastic or other suitable material. The dental device 100 may include a flexible material such as silicon rings 64 and 65 or rubber. The dental device 100 may include both a rigid material and a flexible material. The dental device 100 may have a diameter ranging from 3.0 mm to 6.0 mm.

The distal part 5 has a screw thread 51 on the outer surface and one or a plurality of lateral holes 11 disposed at near the distal end 10. The lateral holes 11 communicate to the central lumen 12. Therefore, a liquid may be drained through the lateral holes 11 and the central lumen 12 and injected through the central lumen 12 and the lateral holes 11. The screw thread 51 may be extended around the lateral holes 11 but is disconnected by the lateral holes 11. The lateral holes 11 may be two holes disposed opposite of each other but may be three or more holes. The lateral holes 11 may have a shape of a circle, an oval, a square or a square with rounded corners. Diameter of the distal part 5 is smaller around the distal end 10 and the lateral holes 11 than the other portion. Therefore, the distal end 10 and the lateral holes 11 do not touch the side wall of osteotomy when the dental device 100 advances through the osteotomy. The distal part 5 around the lateral holes 11 is rounded to form a non-cutting edge. The screw thread 51 is also gently trimmed around the lateral holes 11. Accordingly, no bone shaving is occurred around the lateral holes 11 when the dental device 100 rotates through the osteotomy. The size and position of the lateral holes 11 may be varied but the lateral holes 11 are generally disposed at about 1 mm~5 mm from the distal end 10.

The proximal part 7 has a plurality of loop protrusions 71 on the outer surface. The loop protrusions 71 may have asymmetric slopes. The slope of the distal end side is steeper than the slope of the proximal end side. The loop protrusions 71 provide a tight and retentive connection with a medical tube. However, the loop protrusions 71 are optional. Therefore, the proximal part 7 may have a smooth surface without the loop protrusions 71. The proximal part 7 has a proximal end 13 at which the entrance of the central lumen 12 is disposed.

The middle part 6 is disposed between the distal part 5 and the proximal part 7. The middle part 6 may include multiple sided nut portions 62 and 63, silicon rings 64 and 65, and a stopper protrusion 61. The stopper protrusion 61 is formed of a loop protrusion having a larger diameter than the other portions of the dental device 100. The stopper protrusion 61 provides a lower limit of a stopper (not illustrated) through which the distal part 5 is inserted. The stopper is a separate device to restrict insertion length of the distal part 5 into the osteotomy. Length of the stopper may range from 3 mm to 12 mm. The silicon ring 65 prevents the stopper from slipping out from the dental device 100 and temporarily fixes position of the stopper. The silicon ring 65 is put on a groove formed between the distal part 6 and the stopper protrusion 61.

Two multiple sided nut portions 62 and 63 are disposed with a groove therebetween. The silicon ring 64 is put on the groove. The multiple sided nut portions 62 and 63 are inserted into an adapter of a ratchet wrench when the dental device 100 is screwed though the osteotomy. At this time, the silicon ring 64 prevents the adapter from slipping out from the multiple sided nut portions 62 and 63.

The distal part 5, the middle part 6 and the proximal part 7 is integrally formed in this embodiment. However, some of these three parts 5, 6, and 7 may be separately manufactured and connected by bolt-nut connection.

Insertion depth of the dental device 100 may be controlled by selecting the length of the stopper.

The dental device 100 according to an exemplary embodiment of the present invention may provide an efficient procedure for crestal approach sinus lift technique.

Figure 8:
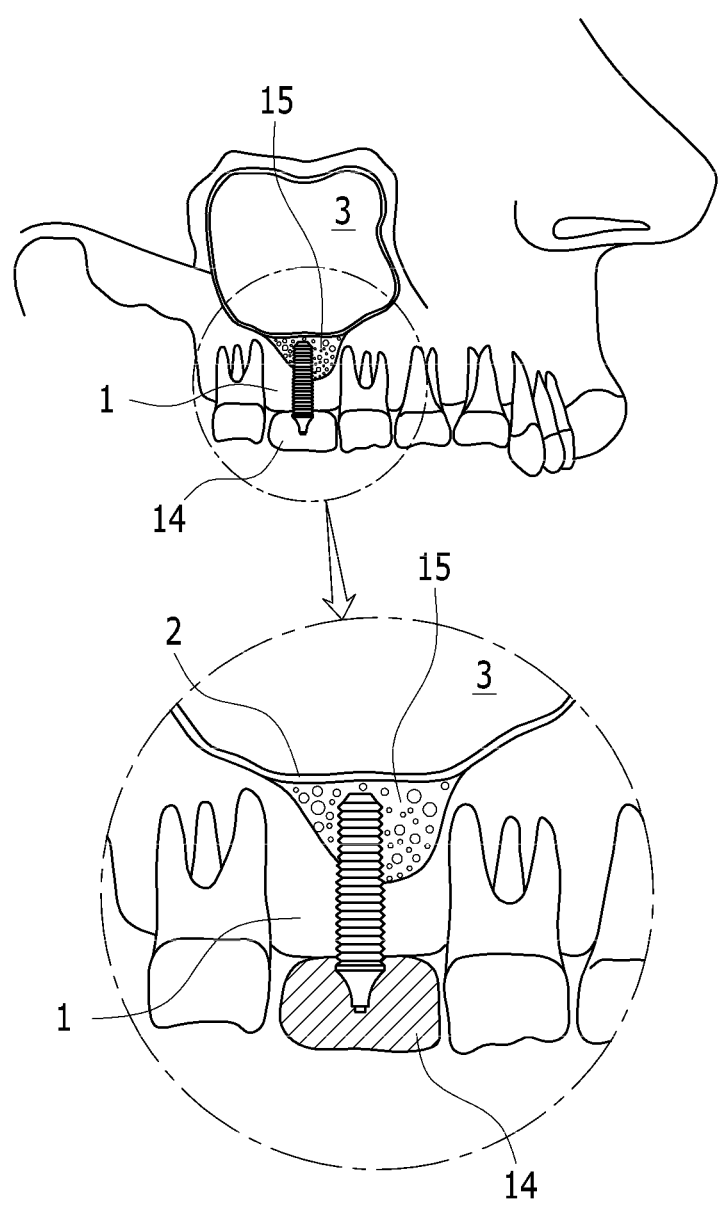
FIG. 8 is a schematic illustration of a surgical procedure for implanting the dental implant using a dental device according to an exemplary embodiment of the present invention.

FIG. 8 is a schematic illustration of a surgical procedure for implanting the dental implant using a dental device according to an exemplary embodiment of the present invention The maxillary sinus 3 is separated from the mouth by the alveolar bone 1. The top of the alveolar bone 1 is covered by the sinus membrane 2. As shown in FIG. 8, the upper surface of the alveolar bone 1 may be depressed at a portion where a dental implant 30 should be located. Therefore, the alveolar bone 1 in the depressed portion is not strong enough to support the dental implant 30 of sufficient length which may be about 8-15 mm. In this case, artificial bone 15 should be generated by the crestal approach sinus lift technique or lateral window technique before implanting the dental implant 30.

Figure 10:
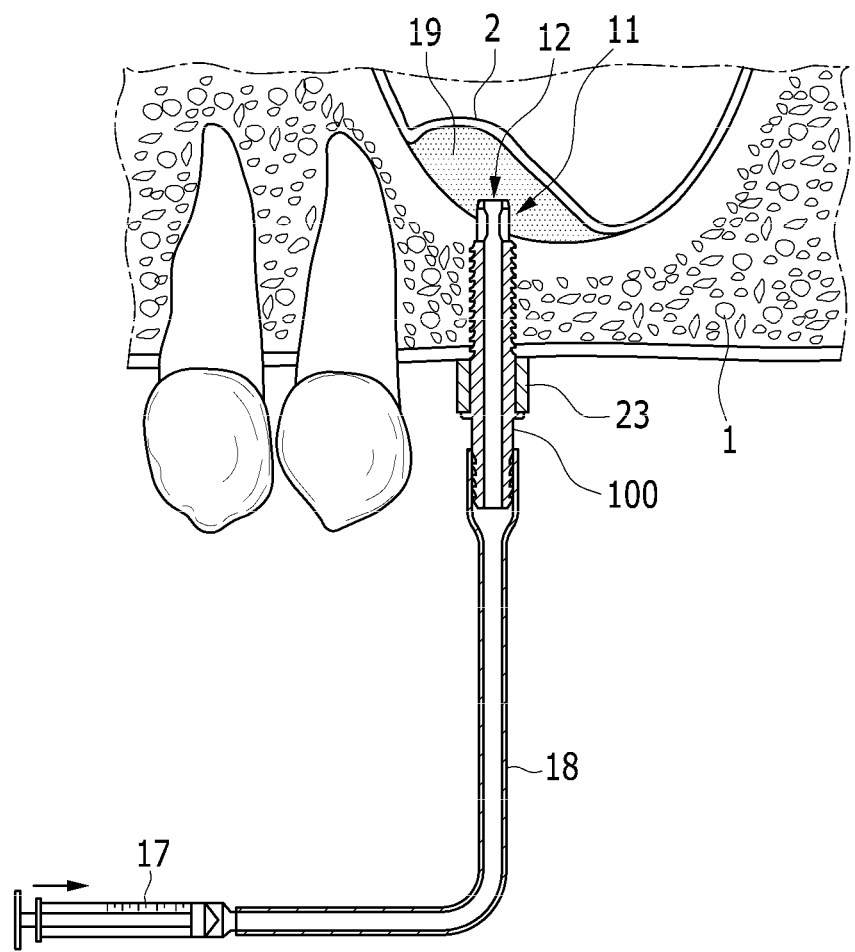
FIGS. 10 and 11 are schematic illustrations of sinus lift surgical procedure using a dental device according to an exemplary embodiment of the present invention.
Figure 11:
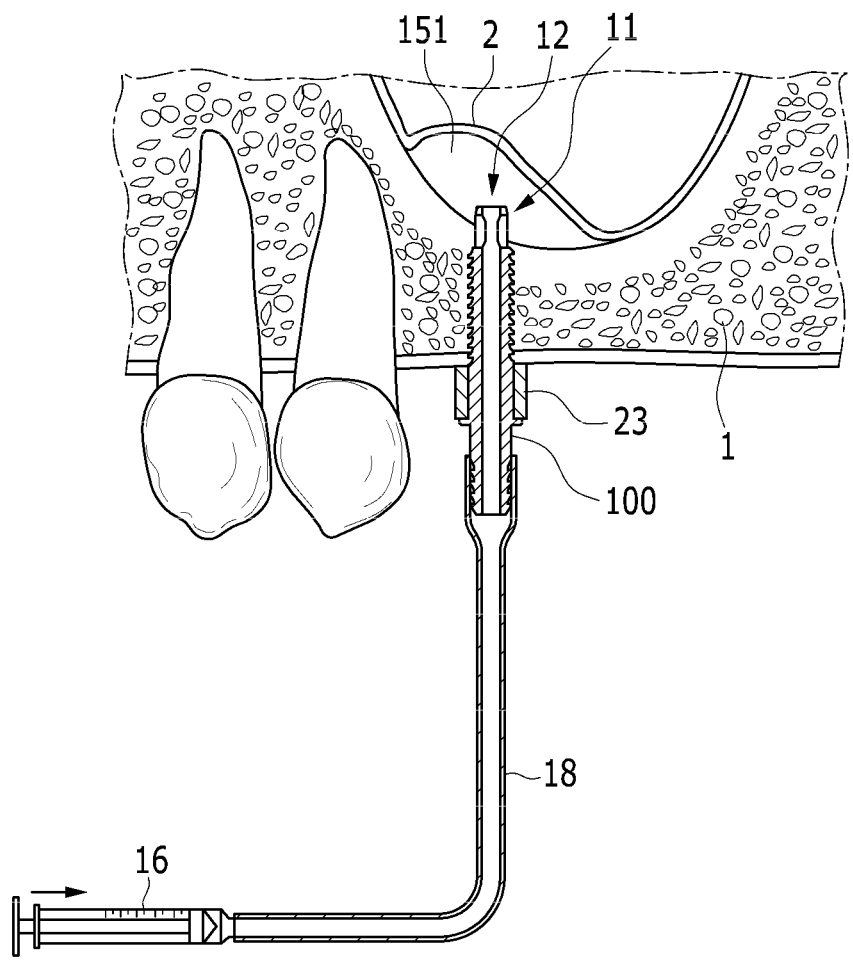

FIGS. 9A-9D are schematic illustrations of several steps of sinus lift surgical procedure using a dental device according to an exemplary embodiment of the present invention. FIGS. 10 and 11 are schematic illustrations of sinus lift surgical procedure using a dental device according to an exemplary embodiment of the present invention.

To generate artificial bone 15 in the maxillary sinus 3 or additionally perform implantation, the following steps are performed.

Figure 9A:
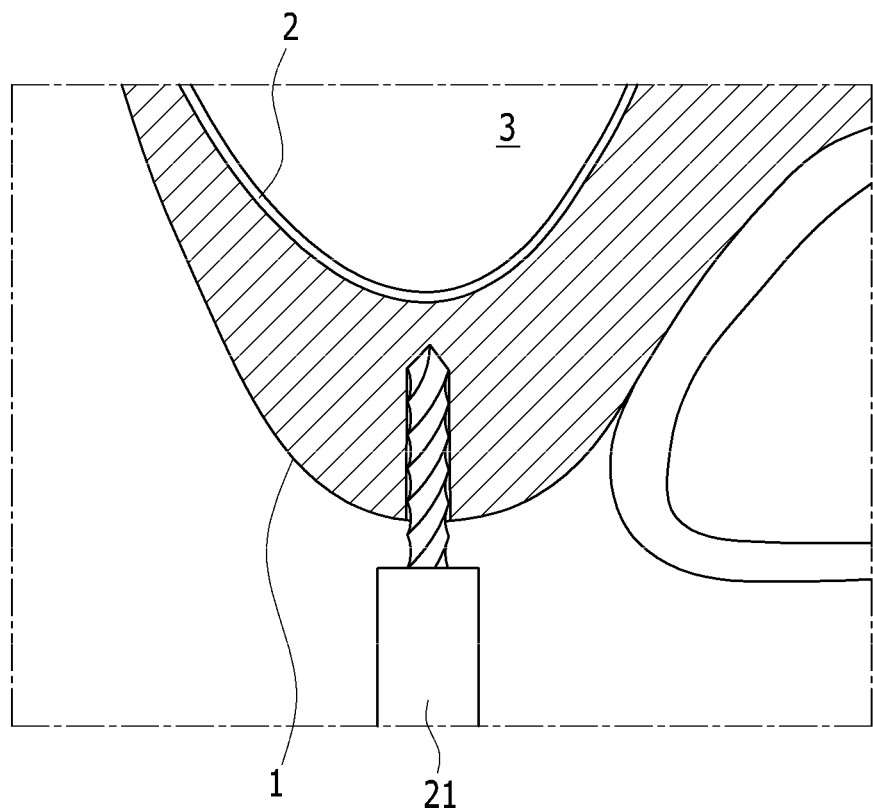
FIGS. 9A-9D are schematic illustrations of several steps of sinus lift surgical procedure using a dental device according to an exemplary embodiment of the present invention.

Referring FIG. 9A, the full thickness of periosteal flap is raised and implant site is marked on the alveolar bone 1 with a marking drill 21.

Figure 9B:
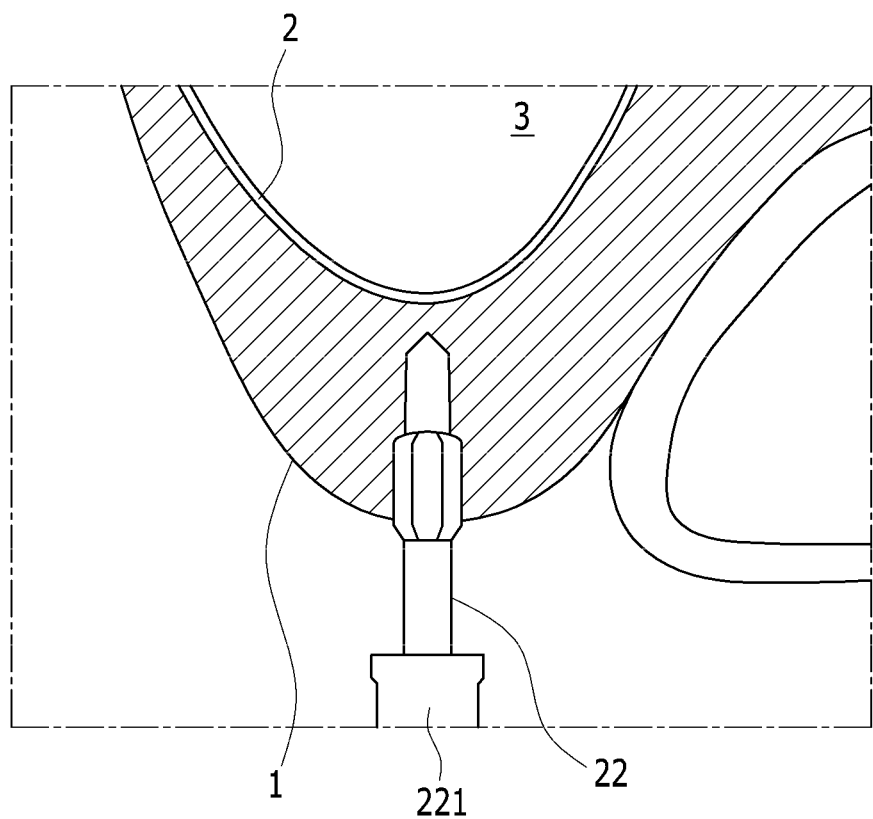
Figure 9C:
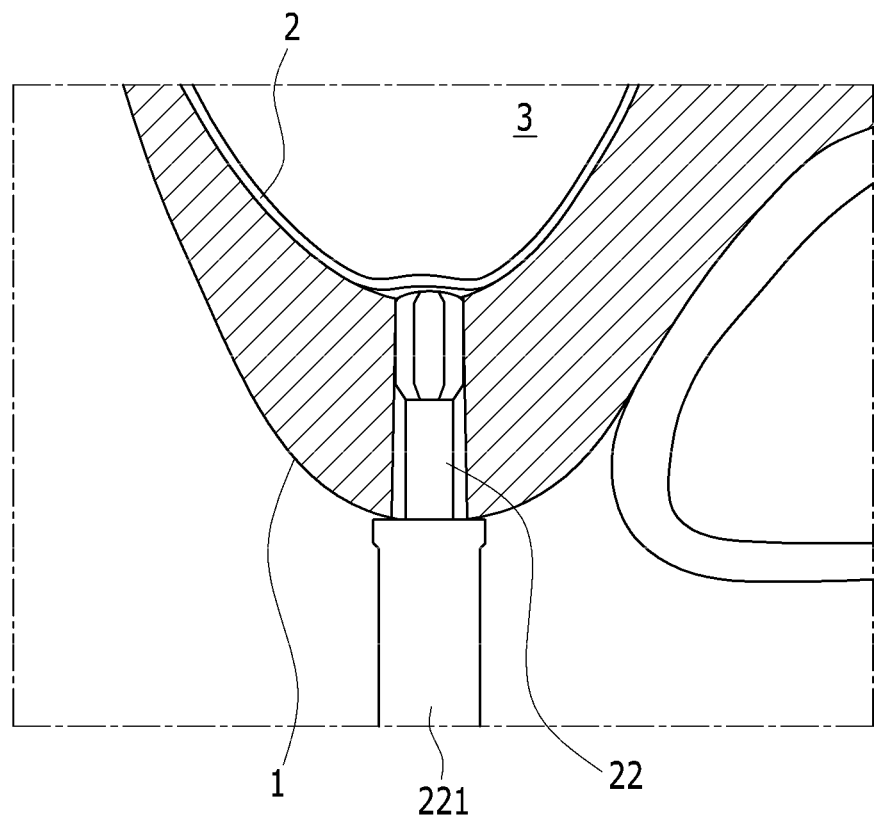

Referring to FIGS. 9B and 9C, the osteotomy is performed using a special drill 22 (e.g. SD Reamer from Surgident. Co.) with a stopper 221. The drill 22 goes all the way to or beyond the sinus floor of the alveolar bone 1 depending on the 3 dimensional morphology of the maxillary sinus 3 without perforating the sinus membrane 2.

Figure 9D:
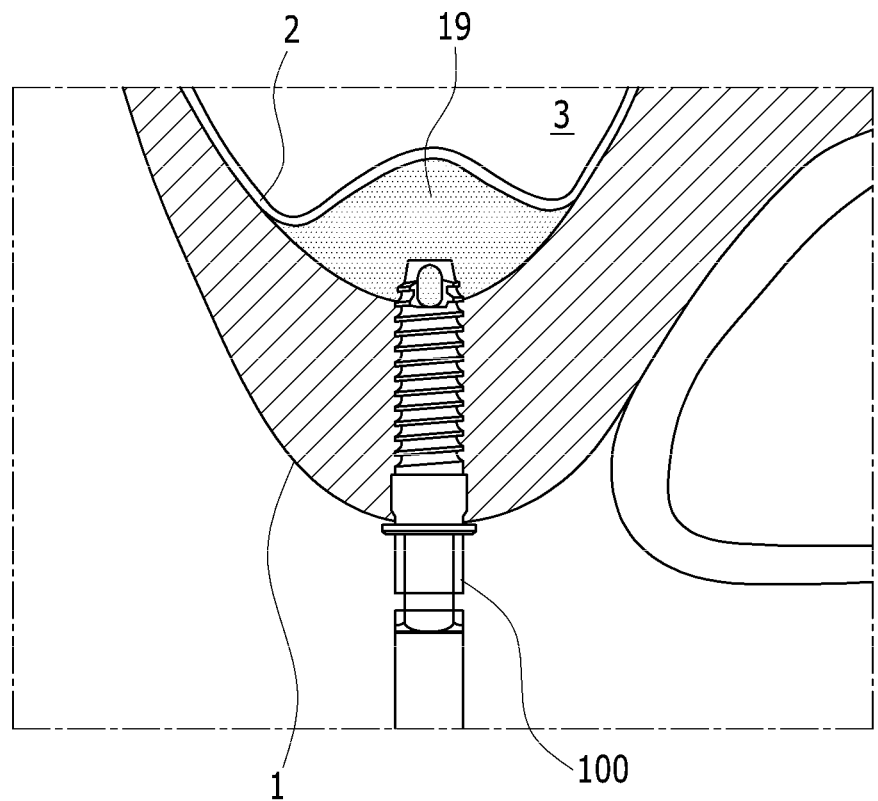

Referring to FIG. 9D, after confirming the sinus membrane 2 is intact, the dental device 100 according to an exemplary embodiment of the present invention is inserted into the osteotomy. The dental device 100 compresses the side wall of the osteotomy as it advances, thereby making water tight seal. Then, a saline solution 19 is injected through the central rumen 12 of the dental device 100 to hydraulically lift the sinus membrane 2.

Referring FIG. 10, for injecting the saline solution 19, the proximal part 7 of the dental device 100 may be connected to a tube 18 which is attached to a syringe 17 or a container that houses the saline solution 19. The saline solution 19 may be substituted with other appropriate fluid for lifting the sinus membrane 2. The appropriate fluid may be a liquid or a fluidal solid. FIG. 10 illustrates that a stopper 23 is put on the dental device 100 to control the insertion depth of the dental device 100.

Before connecting the tube 18 to the proximal part 7 of the dental device 100, the operator may first draw the saline solution 19 into the syringe 17. A short section of the tube 18 is typically pre-connected to the tip of the syringe 17 before the operator draws the saline solution 19.

With the distal end of the tube 18 being elevated, the operator may advance the plunger of the syringe 17 to release excess saline solution 19 out of the exit orifices until only the desired amount of the saline solution 19 remains within the syringe 17 for delivery into the maxillary sinus as indicated by the plunger's position relative to the graduated scale. The saline solution 19 will also remain within the tube 18.

The distal end of the tube 18 is then connected to the proximal part 7 of the dental device 100.

The plunger of the syringe 17 may then be smoothly pressed to introduce the desired amount of the saline solution 19 above the sinus floor. The sinus membrane 2 may be initially raised and separated from the floor of the maxillary sinus 3 by the distal end 10 of the dental device 100. The distal end 10 of the dental device 100 may have a smooth surface not to cut the sinus membrane 2. The sinus membrane 2 is further raised by hydraulic pressure of the saline solution 19 to create a cavity.

An appropriate amount of the saline solution 19 is introduced under the sinus membrane 2 so that the sinus membrane 2 is elevated between 4 mm to 10 mm to provide a total vertical bone height of 8 mm to 14 mm.

One of complication in sinus lift procedure is perforation of the sinus membrane 2.

The operator can evaluate condition of the sinus membrane 2 by comparing introduced amount of the saline solution 19 to drained amount of the saline solution 19. If the saline solution 19 has not been lost through a perforation of the sinus membrane 2, the drained saline solution 19 should approximately match the amount of the saline solution 19 that had been introduced from the syringe.

The lateral hole 11 of the dental device 100 facilitates the draining of the saline solution 19. Referring to FIG. 10, if the sinus floor is sloped, the distal end 10 of the dental device 100 should be raised enough above the sinus floor to introduce the saline solution 19. At this time, if the lateral hole 11 is not provided, the saline solution 19 will not be completely drained but may remain blow the distal end 10 of the dental device 100. However, the dental device 100 according to an exemplary embodiment of the present invention has the lateral hole 11. Therefore, the saline solution 19 may be easily and completely drained through the lateral hole 11. Accordingly, condition of the sinus membrane 2 may be evaluated by comparing introduced amount of the saline solution to drained amount of the saline solution.

Referring to FIG. 11, after draining the saline solution 19 and evaluating the condition of the sinus membrane 2, without removing the dental device 100, the syringe 17 that has drained the saline solution 19 is changed to a different syringe 16 containing a bone regenerative material 151. The regenerative material 151 is composed of a fluid substance.

The regenerative material 151 is injected through the dental device 100 to fill the space formed by of the hydraulic lifting of the sinus membrane 2.

After the regenerative material 151 is injected, the dental device 100 may be extracted from the osteotomy and a dental implant may be implanted through the osteotomy. However, the procedure may be finished without the implantation.

This procedure can save significant amount of time in comparison with the prior method that removes the lifting device after lifting the sinus membrane, drains the saline solution and places bone graft materials into the bone bore.

While this invention has been described in connection with what is presently considered to be practical exemplary embodiments, it is to be understood that the invention is not limited to the disclosed embodiments, but, on the contrary, is intended to cover various modifications and equivalent arrangements included within the spirit and scope of the appended claims.

What is claimed is:

1. A dental device comprising:
   a distal part having a first lateral hole formed on a lateral side of the distal part;
   a middle part connected to the distal part; and
   a proximal part connected to the middle part,
   wherein the dental device has a central lumen penetrating the proximal part, the middle part, and the distal part and communicating to the first lateral hole,
   wherein the distal part has an exit of the central lumen at a distal end and the proximal part has an entrance of the central lumen at a proximal end, and
   wherein the first lateral hole penetrates the lateral side of the distal part to form a first lateral exit of the central lumen so as to allow a liquid to drain through the first lateral hole.

2. The dental device of claim 1, wherein the distal part further has a second lateral hole disposed opposite to the first lateral hole and communicating to the central lumen and
   wherein the second lateral hole penetrates the lateral side of the distal part to form a second lateral exit of the central lumen.

3. The dental device of claim 2, wherein the distal part comprises a screw thread on an outer surface of the distal part.

4. The dental device of claim 2, wherein the first and second lateral holes have a shape among a circle, an oval, a square and a square with rounded corners.

5. The dental device of claim 2, wherein diameter of the distal part is smaller around the distal end and the first and second lateral holes than the other portion.

6. The dental device of claim 2, wherein the distal part around the first and second lateral holes is rounded or gently trimmed to form a non-cutting edge.

7. The dental device of claim 2, wherein the first and second lateral holes are disposed in 1 mm~5 mm from the distal end.

8. The dental device of claim 1, wherein the proximal part has a plurality of loop protrusions on an outer surface of the proximal part.

9. The dental device of claim 8, wherein the loop protrusions have asymmetric slopes.

10. The dental device of claim 1, wherein the middle part comprises at least one multiple sided nut portion and a stopper protrusion.

11. The dental device of claim 10, wherein the stopper protrusion has a larger diameter than the other portions of the dental device and is disposed closer from the distal part than the at least one multiple sided nut portion.

12. The dental device of claim 11, wherein the middle part comprises two multiple sided nut portions and a first groove disposed between the two multiple sided nut portions.

13. The dental device of claim 12, further comprising a first silicon ring put on the first groove.

14. The dental device of claim 11, further comprising a second silicon ring put on a second groove disposed between the distal part and the stopper protrusion.

15. The dental device of claim 1, wherein the distal part, the middle part, and the proximal part are integrally formed.

16. A dental device comprising:
   a distal part having a plurality of lateral holes formed on a lateral side of the distal part and a screw thread formed on an outer surface of the distal part;
   a middle part connected to the distal part and having a stopper protrusion and at least one multiple sided nut portion; and
   a proximal part connected to the middle part,
   wherein the dental device has a central lumen penetrating the proximal part, the middle part, and the distal part and communicating to the plurality of lateral holes and
   wherein the plurality of lateral holes penetrate the lateral side of the distal part to form lateral exits of the central lumen so as to allow a liquid to drain through the plurality of lateral holes.

* * * * *